(12) United States Patent
Zipper

(10) Patent No.: US 8,993,829 B2
(45) Date of Patent: Mar. 31, 2015

(54) DEVICE AND METHOD FOR SECURING SUTURES AND THE LIKE

(76) Inventor: Ralph Zipper, Melbourne, FL (US)

( * ) Notice: Subject to any disclaimer, the term of this patent is extended or adjusted under 35 U.S.C. 154(b) by 1458 days.

(21) Appl. No.: 12/393,067

(22) Filed: Feb. 26, 2009

(65) Prior Publication Data

US 2009/0216271 A1    Aug. 27, 2009

Related U.S. Application Data

(60) Provisional application No. 61/067,265, filed on Feb. 27, 2008.

(51) Int. Cl.
| | |
|---|---|
| *A61K 9/70* | (2006.01) |
| *A61L 15/00* | (2006.01) |
| *A61F 13/00* | (2006.01) |
| *A61F 15/00* | (2006.01) |
| *A61M 35/00* | (2006.01) |
| *A61F 13/02* | (2006.01) |
| *A61B 17/04* | (2006.01) |
| *A61B 17/06* | (2006.01) |
| *A61B 19/08* | (2006.01) |
| *A61B 19/10* | (2006.01) |

(52) U.S. Cl.
CPC ....... *A61B 17/0487* (2013.01); *A61B 17/06061* (2013.01); *A61B 2019/085* (2013.01); *A61B 2019/103* (2013.01); *A61B 2019/106* (2013.01)
USPC ............... 602/43; 424/443; 424/445; 602/42; 602/52; 602/54; 602/78; 604/289; 604/304; 604/307; 604/308

(58) Field of Classification Search
USPC .............. 602/3, 41–59, 75, 78; 424/443, 445; 604/289, 304, 307, 308
See application file for complete search history.

(56) References Cited

U.S. PATENT DOCUMENTS

| | | | |
|---|---|---|---|
| 3,430,300 A | 3/1969 | Doan | |
| 3,547,120 A * | 12/1970 | Grossman | 602/59 |
| 3,826,254 A | 7/1974 | Mellor | |
| 3,918,446 A | 11/1975 | Buttaravoli | |
| 4,122,857 A | 10/1978 | Haerr | |
| 4,221,215 A | 9/1980 | Mandelbaum | |
| 4,447,238 A | 5/1984 | Eldridge, Jr. | |
| 4,838,867 A | 6/1989 | Kalt et al. | |
| 4,884,563 A | 12/1989 | Sessions | |
| 4,907,579 A * | 3/1990 | Kum | 602/58 |
| 5,271,745 A | 12/1993 | Fentress et al. | |
| 5,820,578 A | 10/1998 | Johansen | |
| D404,135 S | 1/1999 | Dunshee | |
| 6,099,553 A | 8/2000 | Hart et al. | |

U.S. PATENT DOCUMENTS

| | | | |
|---|---|---|---|
| 6,316,686 B1 | 11/2001 | Byrd | |
| 6,346,653 B1 * | 2/2002 | Sessions et al. | 602/42 |
| 7,108,710 B2 | 9/2006 | Anderson | |
| 7,316,665 B2 * | 1/2008 | Laurent et al. | 604/46 |
| 2005/0273029 A1 * | 12/2005 | Harris et al. | 602/60 |
| 2009/0062714 A1 * | 3/2009 | Trujillo et al. | 602/54 |

* cited by examiner

*Primary Examiner* — Alireza Nia
*Assistant Examiner* — Brandon L Jackson
(74) *Attorney, Agent, or Firm* — Stephen C. Thomas; Robert A. Lynch

(57) ABSTRACT

A bandage and method for securing a tension member comprising a central body and a plurality of tabs disposed about the central body. A tension member may be disposed across or through a slit or aperture of the central body. A body adhesive on the lower surface of the central body may secure the bandage to the patient. The tension member may then be pulled across the upper surface of the central body and a first tab may be folded over and adhered to the tension member and central body. The tension member may then be pulled back across the first tab and a second tab may be folded over and adhered to the tension member and first tab. Likewise, the tension member may then be pulled back across the second tab and a third tab may be folded over and adhered to the tension member and second tab.

10 Claims, 6 Drawing Sheets

DEVICE AND METHOD FOR SECURING SUTURES AND THE LIKE

CROSS REFERENCE TO RELATED APPLICATIONS

This application claims the benefit of provisional patent application Ser. No. 61/067,265, filed with the USPTO on Feb. 27, 2008, which is herein incorporated by reference in its entirety.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISK

Not applicable.

BACKGROUND OF THE INVENTION

1. Field of the Invention

The present invention generally relates to bandages, more specifically, the present invention relates to bandages for temporarily securing sutures and the like.

2. Background Art

The invention generally relates to holders for a variety of implements and devices including but not limited to sutures and medical tubing, such as vacuum tubes, electrical cords, and the like, which are often employed in surgical operations.

Catheters and needles are commonly inserted into arteries or veins, as for example during cannulation and dialysis. Traditionally, such devices have been attached to patient's bodies as by means of several strips of adhesive tape, or by several bandages placed over the exposed extent of the needle or catheter. This technique is objectionable from the standpoints of remnant risk of inadvertent twisting or removal of the device as may occur as the patient changes position, and of time consumed in applying the several strips. No prior device embodies the unusually advantageous features of construction, mode of use and results now afforded by the present invention.

Throughout a hospital, various implements, sutures, tubing, cords, and materials of various types are used in health care operations, particularly during surgery. Often there is a need to be able to temporarily anchor such materials to a patient. After being deposited, the materials must be easily retrievable for further use during the particular operation and, in addition, there is a need to improve the ability of the physician or nurse involved in the operation to control and handle such materials both during an operation and throughout the recovery process. Thus, it is often advantageous that such materials be prevented from sliding about while in use. It is also advantageous to be able to control the amount of holding power and/or tension provided by the anchoring device.

For example, vacuum tubes, which are used to remove accumulating blood or other fluids during surgery, must be readily accessible throughout the operation and yet not be an obstruction. Nasal gastric tubes are inserted into the patient's nostril and are used to siphon fluids from the patient's stomach. There is a need to be able to anchor and adequately control the nasal gastric tubing that extends from the patient's nostrils. If a cautery is employed during an operation, there is a need to be able to anchor and manipulate the cautery cord which extends from the instrument. A further example of tubes which require manipulation or anchoring are the tubes which extend from intravenous bottles that are used to provide nourishment to the patient. Yet still another example may provide for fixation and tension adjustments as applied to slings and other tension-based treatments.

One known prior device has a square support pad with front and back faces. An adhesive is applied to the back surface so that the pad can be affixed to a substrate, such as a surgical drape. The front or upper surface of the pad is made of felt. One portion of the support pad is a rectangular strip which can be wound around a tube. The end of the strip or pad has a Velcro™ pad that is attached to the felt surface, thereby holding the tube in place. The pad may be wound around the tube so as to contact the tube with a portion of the adhesive side or only the felt side of the strip, thereby determining whether the tube is permitted to slide within the strip while being held. Another device is composed of a strip of felt having a roughened Velcro™ flap attached at one end of the strip. Tubing is placed between the felt strip and flap and is secured by pushing the flap down into the felt to effect the Velcro™ lock.

Such devices have several problems since the Velcro™ has a tendency to snag the gloves used by the nurses and surgeons. In addition, the second device has no ability to anchor tubing without permitting it to slide. Moreover, with the first device, in order to affix a tube without permitting slide, the operator must work with a sticky adhesive that can snare the operator's gloves and the like. Finally, these devices do not allow the operator to control the amount of holding power and/or tension to the held materials.

There is, therefore, a need for an effective device that will easily hold various medical implements, sutures, slings, tubing, and the like to prevent such materials from sliding while also allowing for a potential releasable connection providing for tension adjustments to the held material.

U.S. Pat. No. 3,430,300 to M. Doan discloses two embodiments of a fastener for medical tubes wherein the fasteners are fabricated from a unitary strip of adhesive material such as cloth. In one embodiment the strip of material is T-shaped whereby the top of the T is adapted to be folded down to engage the stem of the T for securing it in folded relationship with respect to a medical tube as illustrated in FIGS. 1-3 of said patent. The second embodiment utilizes an elongate strip, the end portion of which is adapted to be folded over a tube and thereafter threaded through a longitudinal slit 37 which is disposed centrally of the strip at a location below the tube for securing the upper portion of the strip to the tube as illustrated in FIGS. 4-7. In each of the embodiments one end portion of each strip is provided with an adhesive for securing the strip to a support at a location which is spaced from the location of the tube, whereby considerable relative movement is provided between the tube and the surface to which the fastener strip is secured.

U.S. Pat. No. 3,834,380 to S. A. Boyd discloses a holder for I.V. injection cannula and tubing in the form of an elongate longitudinally split clamping tube 20 which is either molded integrally with or adhesively secured transversely to the upper surface of a length of tape. The split clamping tube is adapted to receive a catheter tube or the like after which the clamping tube is closed onto the catheter tube by means of interlocking pads 23 and 24 of artificial burr material 23 and 24 or by means of strap fasteners. Pads 23 and 24 are secured to and carried by an adhesive strip the lower surface of which is adapted to be fastened to the body of a patient by means of adhesive on the lower surface of said strip.

U.S. Pat. No. 3,146,778 to H. A. Krawiec discloses a catheter support which comprises a catheter-holding element 1 and a separate supporting member 10 which latter member is adhesively secured to the skin of a patient. The catheter-holding element is releasably attached to the supporting material by means of a strap fastener for securing tubing in such a manner that considerable relative movement can occur between the tube and the skin of a patient.

U.S. Pat. No. 3,918,446 to P. M. Buttaravoli discloses a securement device for an I.V. catheter and its tubing which comprises a pair of top and bottom pads which are interconnected centrally of their lengths to provide a pair of hinged flaps in the upper pad which overlies the lower pad as illustrated in FIGS. 1-8. The lower pad is provided with elongate slits, notches, and openings for accommodating an infusion needle and medicant. One of the flaps is adapted to secure the coupling portion 50 of a needle whereas the other flap is adapted to anchor a length of tubing which is connected to the coupling portion of a needle to the lower panel. In FIGS. 9-12, a modification is disclosed wherein a single piece of material is provided with an elongate hinge 66 which subdivides the piece into upper and lower portions, said portions being integrally hinged at 60 along mating edges 68 and 70. The lower portion 78 is provided with a notch 81 and openings 82 at opposite ends of through slits 76, as in the lower pad of FIGS. 1-8. The upper portion is adapted to be folded over the lower portion for securing the coupling portion of an infusion needle and I.V. tubing 50, between the pads, by means of an adhesive.

Other devices in the art include the Statlock® Foley Stabilization Device marketed by Bard Medical Division. The tape-free stabilization with a Statlock™ device may provide a lock tight design to prevent pistoning and accidental dislodgement, a swivel design to allow for catheter movement, and a releasable design to allow for easy cleaning of a patient.

Other prior art holders for securement devices known to applicant are embodied in U.S. Pat. No. 2,449,882 to A. J. Daniels; U.S. Pat. No. 3,138,158 to D. W. Gordon et al; U.S. Pat. No. 3,046,984 to F. O. Eby; U.S. Pat. No. 3,286,713 to L. D. Kurtz et al; U.S. Pat. No. 3,683,911 to J. B. McCormick; U.S. Pat. No. 3,724,456 to R. Waxman; U.S. Pat. No. 3,726,280 to A. L. Lacount; U.S. Pat. No. 3,630,195 to L. S. Santomieri; U.S. Pat. No. 3,613,663 to R. P. Johnson; U.S. Pat. No. 3,367,332 to J. N. Groves; U.S. Pat. No. 3,542,321 to R. D. Kahabka; U.S. Pat. No. 3,782,378 to S. J. Page; U.S. Pat. No. 2,814,294 to F. H. J. Figge; U.S. Pat. No. 2,159,947 to I. Gansel; U.S. Pat. No. 2,669,231 to B. Fisher; U.S. Pat. No. 3,677,250 to M. T. Thomas; and U.S. Pat. No. 3,670,727 to D. L. Reiterman.

From these few examples it can be appreciated that anchors, more specifically surgical anchors, are typically time-consuming, difficult to use, hard to place, often unreliable as an effective holding system, difficult to adjust, and impossible to relocate.

BRIEF SUMMARY OF THE INVENTION

It is often necessary to hold a tension member, such as a surgical suture, wire or other material in place at or near the skin. Traditional options include knot tying, the use of beads, the use of tape, and the like. The knot tying may involve penetration of the skin and an associated resultant injury. The placement of a bead or button at the level of the skin often results in point loading or point pressure on the skin with an associated resultant injury. Although tape may hold a suture, wire, or other material in place, tape offers limited retentive strength and undesired movement of the tape is common. All of these undesirable methods and devices are further limited in their adjustability after completion of the medical procedure. Once the suture, wire or material is fixed in place, there is little ability to change the position and fixation of the structure used to hold the tension member.

The present invention provides a new bandage type anchor or fixation device. This device is capable of holding or fixing suture, wire, or other material at or near the skin with no or minimal injury to the skin. The device also allows multiple adjustments of the suture, wire, or other material with repeat subsequent fixation.

The present invention provides a bandage for securing a tension member, comprising a central body for contacting a bodily surface, the central body having an upper surface and a lower surface wherein the lower surface faces and abuts the bodily surface, and a plurality of tabs forming at least one securable connection to the upper surface of the central body, wherein each of the plurality of tabs comprises a first surface and a second surface, wherein the tension member passes over at least a portion of the upper surface of the central body and the first surface of a first tab of the plurality of tabs forms a first securable connection with the upper surface of the central body thereby fixing the tension member between the central body and the first tab.

The present invention further provides a method for securing a tension member, comprising the steps of providing a bandage comprising a central body having a lower surface and a body adhesive disposed thereon for contacting a bodily surface and a plurality of tabs forming at least one securable connection with the central body, wherein a connection element is disposed on a first surface of each of said plurality of tabs, positioning the central body on the bodily surface, passing the tension member over at least a portion of an upper surface of the central body, and placing the first surface of a first tab of the plurality of tabs in physical contact with the upper surface of the central body so that the tension member is disposed between the first surface of the first tab and the upper surface of the central body, wherein the connection element on the first surface of the first tab provides a first securable connection between the central body and the first tab and wherein a second surface of the first tab faces away from the bodily surface when the first securable connection is formed.

DETAILED DESCRIPTION OF THE INVENTION

Figure 1:
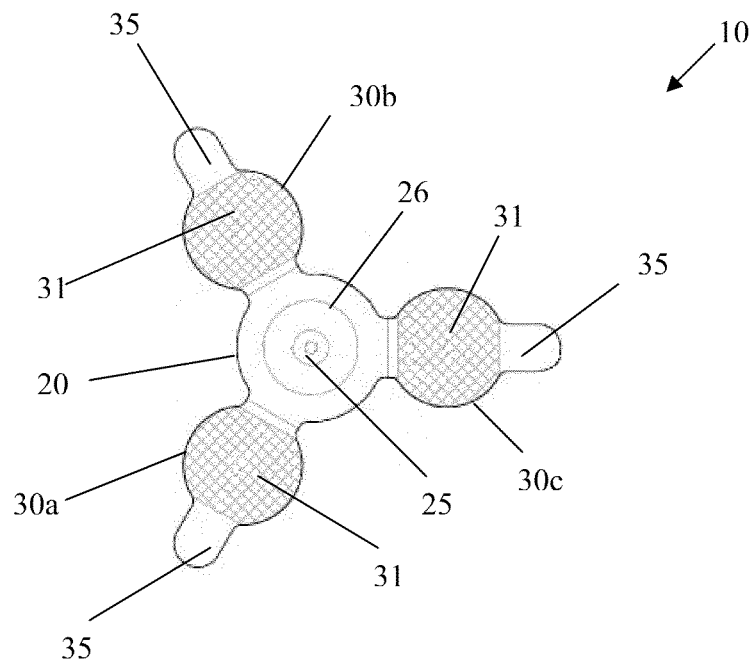
FIG. 1 depicts a top planar view of an embodiment of a bandage of the present invention.
Figure 2:
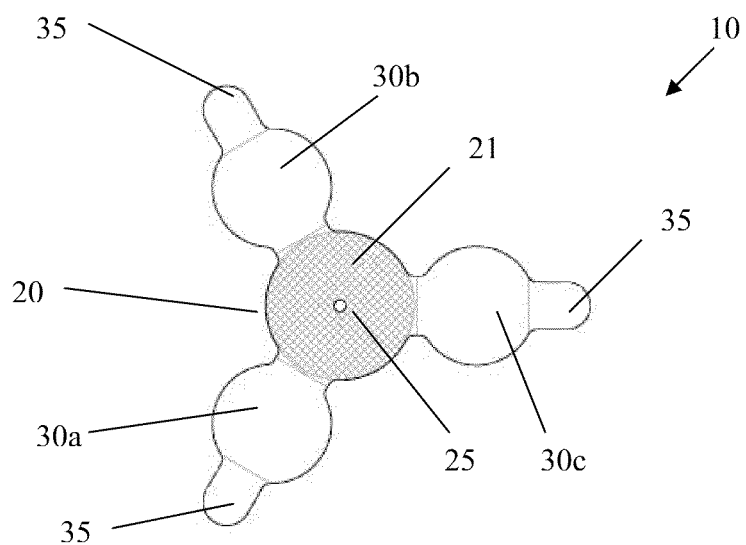
FIG. 2 depicts a bottom planar view of an embodiment of a bandage of the present invention.

As illustrated in FIGS. 1 and 2, the device may be composed of a bandage 10 generally comprising a central body 20 and a plurality of petals, flaps, or tabs 30a-30c. The bandage 10 may provide a means of securing and anchoring a tension member 55 via a tortuous path created between the central body 20 and the plurality of successively overlain tabs 30a-

30c. The tension member 55 may be passed across the central body 20 as well as being passed across each and every successive tab 30a-30c that is secured above thereafter. Such a circuitous path generates sufficient fixation to retain the tension member 55 at skin level. Alternatively, bandages 10 comprising absorbable or biocompatible materials may be used to releasably retain the tension member 55 at or below skin level. Such tension members 55 may include but are not limited to sutures, wires, filaments, and the like.

As shown in FIG. 2, the central body 20 may incorporate a body adhesive 21 disposed on the lower surface of the central body 20 that allows bonding to a bodily surface or to other material on top of the bodily surface. Body adhesive 21 may be either non-releasable adhesive or releasable adhesive, wherein a releasable adhesive allows for relocation of the bandage 10. The central body 20 may also incorporate an optional access point 25 in the form of a hole, a penetration, a slit from a side border, and the like for allowing passage of a tension member 55 through the central body 20. Alternatively, the tension member 55 may be disposed across at least a portion the upper surface of the central body 20 for fixation purposes, as opposed to passing through the central body 20 and thereafter disposing the tension member 55 across only a portion of the central body 20. As depicted in FIG. 1, the upper surface of the central body 20 may include indicia 26, such as high contrast circles and the like, disposed thereon to assist the surgeon in both locating the central body 20 and identifying its center and/or access point 25. Further, the upper surface of the central body 20 may comprise a layer of body adhesive 21 to assist in both tension member 55 fixation and adhesion to tabs 30a-30c disposed thereon.

Additionally, an absorbent material, preferably an absorbent pad, gauze pad, or the like, may be disposed on the bottom surface of the central body 20. Preferably, the absorbent material may be centered on the central body 20 and held in place by the body adhesive 21 layer. The bandage 10 may then be placed on the body surface so that the body adhesive 21 faces the body surface and the absorbent pad is located over a subject wound and associated tension member 55 if applicable. In such an embodiment, the periphery of the lower surface of the central body 20 may comprise exposed adhesive 21 to allow for fixation of the central body 20 to the bodily surface when an absorbent pad is used. In such an embodiment, the access point 25 may be disposed through the central body 20, the absorbent pad, or both.

FIG. 1 depicts the surgeon's side of the present inventive bandage 10 wherein the upper surface of the central body 20 and the first surface of tabs 30a-30c face away from the bodily surface of the patient. The tabs 30a-30c of the bandage 10 may have a connection element 31 on their respective first surfaces and/or second surfaces. This connection element 31 may be a releasable adhesive allowing for release of the tension member 55 to provide for tension adjustments followed by re-securing the tension member 55 within the tabs 30a-30c of the bandage 10. In alternate embodiments, the connection element may also comprise any means of connecting two surfaces known within the art including but not limited to non-releasable adhesive, hook and loop fasteners, and the like. Exemplary adhesives may include but are not limited to double coated polyethylene tape with an acrylate adhesive, white spunlace polyester/rayon blend with an acrylate adhesive, PVC foam with an acrylic co-polymer adhesive, 2 Mil silicone coated PET liner, cross-linked polyethylene foam with a non-sensitizing acrylic adhesive, and the like. FIGS. 1 and 2 illustrate a "petal" configuration of the tabs 30a-30c disposed about the central body 20. In such a preferred embodiment, creases or foldable regions may be located at the junction of the tabs 30a-30c and the central body 20 to facilitate the folding of the respective tabs 30a-30c onto the upper surface of the central body 20. While the Figures depict a preferred embodiment of the bandage 10 having three tabs 30a-30c, the scope of the invention includes a plurality of one or more tabs used to provide a securable connection for a tension member 55 used with a bandage 10 of the present invention.

The tabs 30a-30c of the present invention need not be limited to the "petal" configuration. Tabs 30 may comprise an "accordion" configuration, wherein the central body 20 initiates or represents one end of the "accordion" with a plurality of successive tabs 30 being thereafter attached to each immediately adjacent tab 30 and folded over to comprise a vertically-stacked "accordion" configuration. The tension member 55 may then be pulled across and secured by each successive tab 30 layer of the "accordion" configuration. Alternatively, each of the plurality of tabs 30 may be completely independent from the central body 20 and independent from each other. In this manner, no folding is required since each tab 30 is individually manipulated and disposed so that its first layer is put into direct physical contact with the tension member 55 and the either the upper surface of the central body 20 or the second surface of the previously disposed tab 30. Such a configuration embodies, a "sandwich" stack configuration, wherein the central body 20 initiates the bandage 10 and successive tab 30 layers are disposed thereon after the tension member 55 is passed across the top of each previous layer.

The tabs 30a-30c of the present invention may further comprise at least one extension 35 in communication with and projecting from each respective tab 30a-30c. The extensions 35 are used to assist in the general manipulation, securing, releasing, and folding/unfolding functions of the tabs 30a-30c. A surgeon need only grasp the extension 35 to more easily fold or release the associated tab 30a-30c along its respective crease line or foldable region. Such extensions 35 may be free of connection elements 31, and may be specifically treated with a material to prevent extension 35 adhesion to any surface. Additionally, the extensions 35 or tabs 30a-30c may be labeled with indicia on one or both sides to assist the surgeon in identifying the total number of tab 30a-30c fixation layers being used and/or at which step the surgeon is currently at in the present inventive fixation layering method.

The size and shape of the central body 20 and the tabs 30a-30c may be determined by the amount of retentive force required and the area of the body or skin to which the bandage 10 will be applied. The bandage 10 may further include a bolster piece or pieces (not shown) to assist in supporting the shape and structure of the device. Such a bolster may further serve to disperse the retention force or point loading across the surface area of the central body 20 and provide an improved rigidity or resilience to the central body 20 and/or plurality of tabs 30a-30c.

Figure 3:
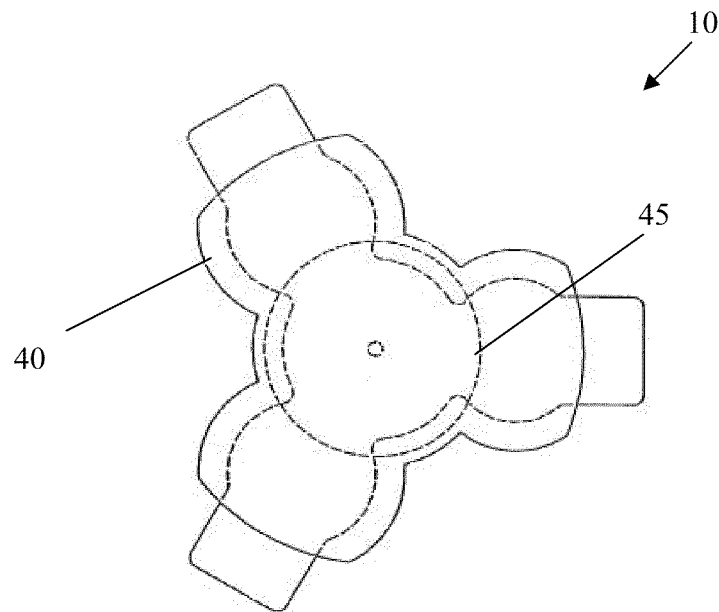
FIG. 3 depicts a top planar view of an embodiment of a bandage of the present invention having adhesive overlays.
Figure 4:
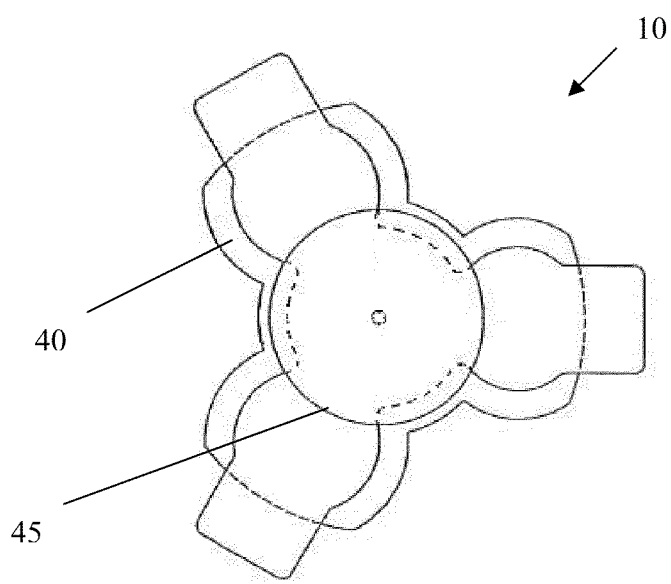
FIG. 4 depicts a bottom planar view of an embodiment of a bandage of the present invention having adhesive overlays.

As depicted in both FIG. 3 (upper surface perspective) and FIG. 4 (lower surface perspective), an upper protective overlay 40 and/or a lower protective overlay 45 may be placed over the upper and lower surfaces of the bandage 10, respectively. The protective overlays 40,45 keep any absorbent material clean and any body adhesives 21 and connection elements 31 covered until application of the bandage 10 is desired. The protective overlays 40,45 enable the bandage 10 to be handled without deterioration and further enable a user to manipulate the bandage 10 without touching the absorbent material, body adhesive 21 or connection elements 31 of the bandage 10. As shown in FIGS. 3 and 4, the protective overlays 40,45 may overlap their covered surfaces, thus providing pulls at their respective peripheral edges that may be grasped between the thumb and index finger and peeled back to expose an absorbent material, adhesive layer 21, and/or connection element 31 there below.

Figure 5A:
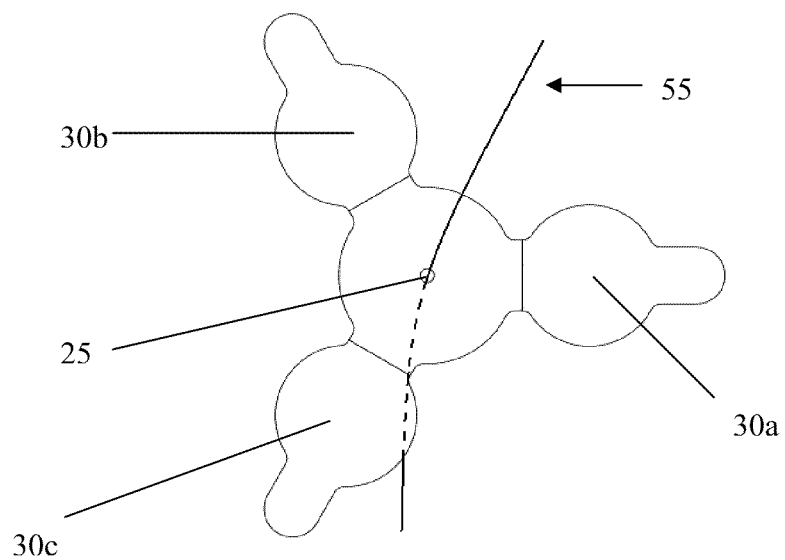
FIGS. 5a-5f depict top planar views of an embodiment of one method of use of the present invention.
Figure 5B:
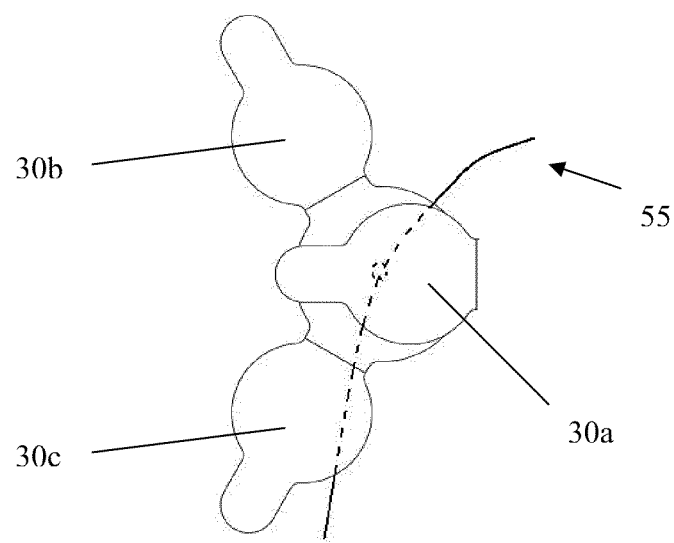
Figure 5C:
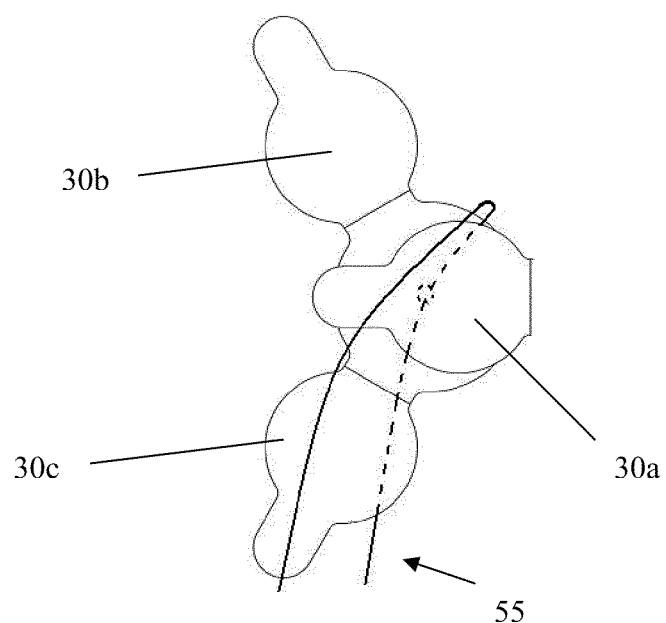
Figure 5D:
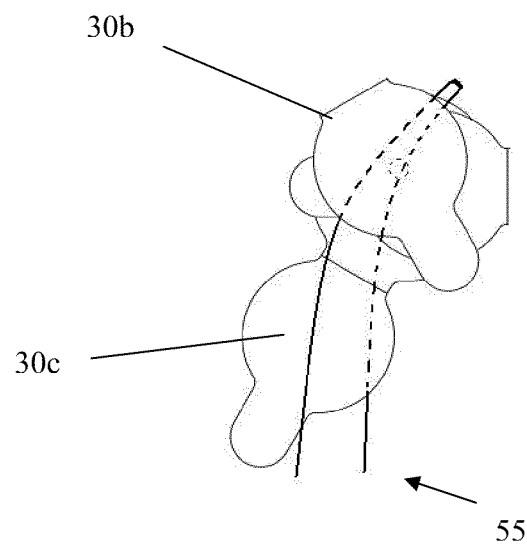
Figure 5E:
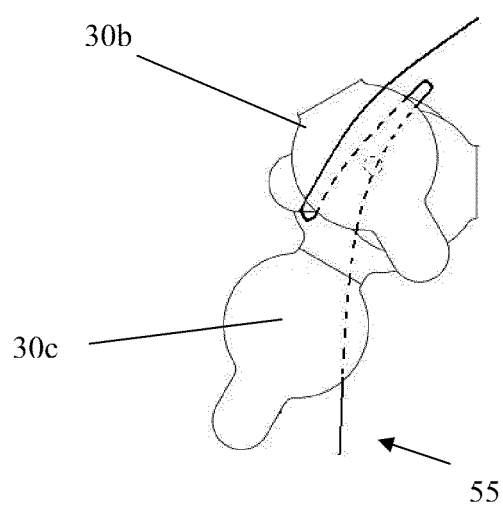
Figure 5F:
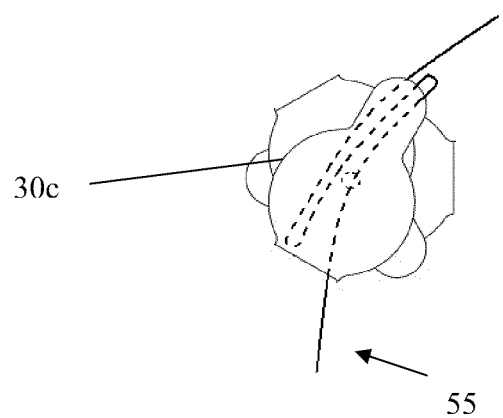

In use, as depicted in FIGS. 5a-5f, one embodiment of the present invention may comprise successive folding of a plurality of tab 30a-30c layers to provide a securing force on the tension member 55. Initially, the optional lower protective overlay 45 may be removed from the lower surface of the central body 20. As shown in FIG. 5a, the tension member 55 may then be passed through an optional access port 25 disposed within the central body 20 and the central body 20 may then be placed upon the appropriate bodily surface. The optional upper protective overlay 40 may then be removed from the central body 20 and/or the plurality of tabs 30a-30c. Alternatively, the access port 25 may be eliminated and the tension member 55 may be disposed across the upper surface of the central body 20 after the central body has been placed upon the bodily surface and the optional upper protective overlay 40 has been removed. As shown in FIG. 5b, a first fold may be created wherein the first tab 30a is folded over at a first foldable region immediately adjacent the central body 20 allowing the first surface of the first tab 30a to come into physical contact with the upper surface of the central body 20 securing the tension member 55 there between. As shown in FIG. 5c, the tension member 55 may then be passed back across the second surface of the first tab 30a. As shown in FIG. 5d, a second fold may be created wherein the second tab 30b is folded over at a second foldable region immediately adjacent the central body 20 allowing the first surface of the second tab 30b to come into physical contact with the second surface of the first tab 30a securing the tension member 55 there between. As shown in FIG. 5e, the tension member 55 may then be passed back across the second surface of the second tab 30b. As shown in FIG. 5f, a third fold may be created wherein the third tab 30c is folded over at a third foldable region immediately adjacent the central body 20 allowing the first surface of the third tab 30c to come into physical contact with the second surface of the second tab 30b securing the tension member 55 there between. All tab 30a-30c connections and points of physical contact described above may comprise releasable connections and beneficially allow for release, adjustment, and fixation of the tension member 55 in either a surgical or post-surgical environment. Alternatively if adjustments are not required, the connections and points of physical contact may comprise non-releasable connections. The scope of the present invention includes any number of successive overlain tabs 30a-30c, with a preferred embodiment of the present invention comprising three tab 30a-30c layers.

The method steps above may further be incorporated and easily adapted to the accordion embodiment and sandwich-style embodiment previously described. In such embodiments, the location of the pertinent foldable regions or the complete elimination of foldable regions may respectively provide for beneficial variations to the devices and methods of the present invention.

Figure 6:
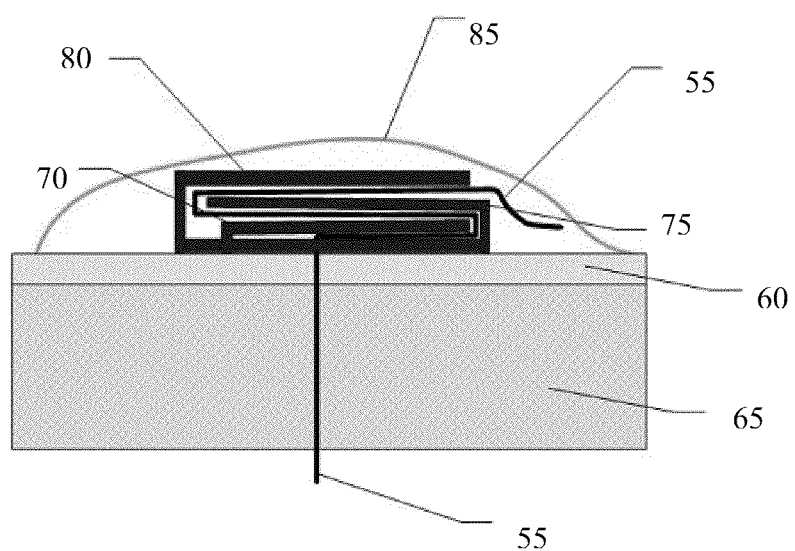
FIG. 6 depicts a side view of an embodiment of a bandage of the present invention retaining a tension member.

FIG. 6 generally depicts a cross section of one embodiment of the present inventive bandage 10 after completion of the above-described method steps. In this particular embodiment, a generic tension member 55 (e.g. suture) is shown exiting a patient's fascia 65 and mucosa or skin 60 and then continues through the access port of the central body. The first tab provides the first fold 70 as the first surface of the first tab folds over the upper surface of the central body. Thereafter, the tension member 55 is passed back across the exposed second surface of the first tab. The second tab provides the second fold 75 as the first surface of the second tab folds over the exposed second surface of the first tab and further secures the tension member 55. Thereafter, the tension member 55 is passed back across the exposed second surface of the second tab. The third tab provides the third fold 80 as the first surface of the third tab folds over the exposed second surface of the second tab and still further secures the tension member 55. An optional top surface tape layer 85 may then be applied and disposed over the present inventive bandage 10 to assist in protection and retention of the securable connections formed therein. As shown in FIG. 6, the tension member 55 is been secured via its circuitous pathway, and anytime thereafter when releasable connections are used the method steps may be reversed to allow for adjustment and re-tensioning of the tension member 55 as needed in a post-surgical setting. The successive securable connections generate the necessary retentive force on the tension member 55 while use of a releasable embodiment of the present inventive bandage 10 allows for unlimited availability of post-surgical adjustments to the tension member 55.

Generally, the design of the present invention allows any suture, wire, line, filament, or any similar material (i.e. tension member) to be releasably or non-releasably held in place. The tension member may make contact with each of the one or more tabs, petals, or flaps of the device. The steps of formation of a circuitous retention device of the present invention may be repeated as necessary and include folding one tab over the tension member, draping the tension member back over the central portion of the device, folding the next tab over the draped tension member, and repeating this draping and folding pattern until all tabs or at least a sufficient number of tabs capable of providing fixation have been folded or otherwise placed into contact with the tension member.

While most of the described embodiments illustrate the device in use as a bandage in a medical setting, the scope of the present invention is not so limited. The fixation device of the present invention may be used to secure lines, wires, strings, filaments, and the like which may be found in a limitless number of non-medical environments. The fixation device of the present invention allows the chosen tension member to be secured, while retaining the ability to release, adjust, and then re-secure the tension member after its tension has been properly adjusted. Such an adjustable and reusable means of fixation provides a much needed benefit across a wide range of technical arts. Alternatively, when there is no need for adjustments to the tension member, the securable connections of the present invention may be formed by non-releasable connections providing for secure and/or permanent fixation of the tension member.

While the above description contains much specificity, these should not be construed as limitations on the scope of any embodiment, but as exemplifications of the presently preferred embodiments thereof. Many other ramifications and variations are possible within the teachings of the various embodiments.

Thus, the scope of the invention should be determined by the appended claims and their legal equivalents, and not by the examples given.

What is claimed is:
1. A bandage for securing a tension member, comprising:
a central body for contacting a bodily surface, wherein said central body comprises a lower surface having a body adhesive thereon for contacting said bodily surface;
a plurality of tabs with each of said plurality of tabs having a first surface and a second surface, wherein a connection element is disposed on said first surface of each of said plurality of tabs, at least one of said plurality of tabs forming a securable connection to said upper surface of said central body;

wherein said tension member passes over at least a portion of said upper surface of said central body and said first surface of a first tab of said plurality of tabs is then disposed in physical contact with said upper surface of said central body forming a first securable connection wherein said tension member is secured between upper surface of said central body and said first surface of said first tab, wherein said tension member then passes across said second surface of said first tab and said first surface of a second tab is then disposed in physical contact with said second surface of said first tab forming a second securable connection wherein said tension member is secured between said second surface of said first tab and said first surface of said second tab, wherein said tension member then passes across said second surface of said second tab and said first surface of a third tab is then disposed in physical contact with said second surface of said second tab forming a third securable connection wherein said tension member is secured between said second surface of said second tab and said first surface of said third tab.

2. The bandage of claim 1, wherein at least a portion of said lower surface of said central body further comprises an absorbent material for cushioning contact with said bodily surface.

3. The bandage of claim 1, wherein said at least one securable connection is releasable and allows for adjustments to said tension member.

4. The bandage of claim 1, wherein said central body further comprises a bolster for providing added rigidity to said central body of said bandage.

5. A bandage for securing a tension member, comprising:
a central body for contacting a bodily surface or a material on top of a bodily surface, said central body having an upper surface and a lower surface wherein said lower surface faces and abuts said bodily surface or material on top of a bodily surface; and
a plurality of tabs forming at least one securable connection to said upper surface of said central body, wherein each of said plurality of tabs comprises a first surface and a second surface;
wherein said tension member passes over at least a portion of said upper surface of said central body and said first surface of a first tab of said plurality of tabs forms a first securable connection with said upper surface of said central body thereby fixing said tension member between said central body and said first tab, and
wherein said tension member is then passed across said second surface of said first tab and said first surface of a second tab of said plurality of tabs forms a second securable connection with said second surface of said first tab thereby fixing said tension member between said first tab and said second tab, and
wherein said tension member is then passed across said second surface of said second tab and said first surface of a third tab of said plurality of tabs forms a third securable connection with said second surface of said second tab thereby fixing said tension member between said second tab and said third tab.

6. A bandage for securing a tension member, comprising:
a central body for contacting a bodily surface or a material on top of a bodily surface, said central body having an upper surface and a lower surface wherein said lower surface faces and abuts said bodily surface or material on top of a bodily surface; and
a plurality of tabs forming at least one securable connection to said upper surface of said central body, wherein each of said plurality of tabs comprises a first surface and a second surface;
wherein said tension member passes over at least a portion of said upper surface of said central body and said first surface of a first tab of said plurality of tabs forms a first securable connection with said upper surface of said central body thereby fixing said tension member between said central body and said first tab, and
wherein said central body further comprises an access point, wherein said tension member passes through said central body via said access point and said tension member then passes over said at least a portion of said upper surface of said central body.

7. A bandage for securing a tension member, comprising:
a central body for contacting a bodily surface or a material on top of a bodily surface, said central body having an upper surface and a lower surface wherein said lower surface faces and abuts said bodily surface or material on top of a bodily surface; and
a plurality of tabs forming at least one securable connection to said upper surface of said central body, wherein each of said plurality of tabs comprises a first surface and a second surface;
wherein said tension member passes over at least a portion of said upper surface of said central body and said first surface of a first tab of said plurality of tabs forms a first securable connection with said upper surface of said central body thereby fixing said tension member between said central body and said first tab, and
wherein a body adhesive is disposed on at least said lower surface of said central body for maintaining said central body in contact with said bodily surface.

8. A bandage for securing a tension member, comprising:
a central body for contacting a bodily surface or a material on top of a bodily surface, said central body having an upper surface and a lower surface wherein said lower surface faces and abuts said bodily surface or material on top of a bodily surface; and
a plurality of tabs forming at least one securable connection to said upper surface of said central body, wherein each of said plurality of tabs comprises a first surface and a second surface;
wherein said tension member passes over at least a portion of said upper surface of said central body and said first surface of a first tab of said plurality of tabs forms a first securable connection with said upper surface of said central body thereby fixing said tension member between said central body and said first tab, and
wherein each of said plurality of tabs further comprises at least one extension projecting from each of said plurality of tabs.

9. A bandage for securing a tension member, comprising:
a central body for contacting a bodily surface or a material on top of a bodily surface, said central body having an upper surface and a lower surface wherein said lower surface faces and abuts said bodily surface or material on top of a bodily surface; and
a plurality of tabs forming at least one securable connection to said upper surface of said central body, wherein each of said plurality of tabs comprises a first surface and a second surface;
wherein said tension member passes over at least a portion of said upper surface of said central body and said first surface of a first tab of said plurality of tabs forms a first securable connection with said upper surface of said central body thereby fixing said tension member between said central body and said first tab, and wherein each of said plurality of tabs further comprises a connection element disposed on said first surface of each of said plurality of tabs for forming said at least one securable connection.

10. A method for securing a tension member, comprising the steps of:

providing a bandage comprising a central body having a lower surface and a body adhesive disposed thereon for contacting a bodily surface and a plurality of tabs forming at least one securable connection with said central body, wherein a connection element is disposed on a first surface of each of said plurality of tabs;

positioning said central body on said bodily surface;

passing said tension member over at least a portion of an upper surface of said central body;

placing said first surface of a first tab of said plurality of tabs in physical contact with said upper surface of said central body so that said tension member is disposed between said first surface of said first tab and said upper surface of said central body, wherein said connection element on said first surface of said first tab provides a first securable connection between said central body and said first tab and wherein a second surface of said first tab faces away from said bodily surface when said first securable connection is formed;

passing said tension member over at least a portion of said second surface of said first tab;

placing said first surface of a second tab of said plurality of tabs in physical contact with said second surface of said first tab so that said tension member is disposed between said first surface of said second tab and said second surface of said first tab, wherein said connection element on said first surface of said second tab provides a second securable connection between said first tab and said second tab and wherein a second surface of said second tab faces away from said bodily surface when said second securable connection is formed;

passing said tension member over at least a portion of said second surface of said second tab; and placing said first surface of a third tab of said plurality of tabs in physical contact with said second surface of said second tab so that said tension member is disposed between said first surface of said third tab and said second surface of said second tab, wherein said connection element on said first surface of said third tab provides a third securable connection between said second tab and said third tab and wherein a second surface of said third tab faces away from said bodily surface when said third securable connection is formed.

* * * * *